(12) United States Patent
Rushton

(10) Patent No.: US 8,460,226 B2
(45) Date of Patent: Jun. 11, 2013

(54) ORTHOTIC DEVICE AND METHOD OF USE

(76) Inventor: Michael James Rushton, Baker City, OR (US)

( * ) Notice: Subject to any disclaimer, the term of this patent is extended or adjusted under 35 U.S.C. 154(b) by 333 days.

(21) Appl. No.: 12/413,892

(22) Filed: Mar. 30, 2009

(65) Prior Publication Data

US 2010/0249686 A1     Sep. 30, 2010

(51) Int. Cl.
    *A61F 5/00*         (2006.01)
(52) U.S. Cl.
    USPC .............................................. 602/23; 602/30
(58) Field of Classification Search
    USPC ............ 602/23, 30, 32, 5; 128/882, 892–894
    See application file for complete search history.

(56) References Cited

U.S. PATENT DOCUMENTS

| 2,416,823 | A  | * | 3/1947  | Day .................................. 602/30 |
| 5,921,243 | A  | * | 7/1999  | Shakoor ......................... 128/882 |
| 6,141,801 | A  | * | 11/2000 | Helenick ............................ 2/159 |
| 6,234,988 | B1 | * | 5/2001  | Brother et al. ................... 602/65 |
| 6,694,641 | B1 | * | 2/2004  | Gill ................................ 36/11.5 |
| 7,234,251 | B2 | * | 6/2007  | Fuerst et al. ................... 36/77 R |

* cited by examiner

*Primary Examiner* — Michael A. Brown
(74) *Attorney, Agent, or Firm* — J. Todd Rushton

(57) ABSTRACT

An orthotic apparatus positioned on the top of the forefoot that aligns and locks the first metatarsal in a plantarflexed position. A compressible orthotic pad positioned on the forefoot directly over the first metatarsal. When pressure is applied to the orthotic pad, the first metatarsal is forced down, unlocking the first metatarsal phalangeal joint and eliminating functional hallux limitus.

19 Claims, 4 Drawing Sheets

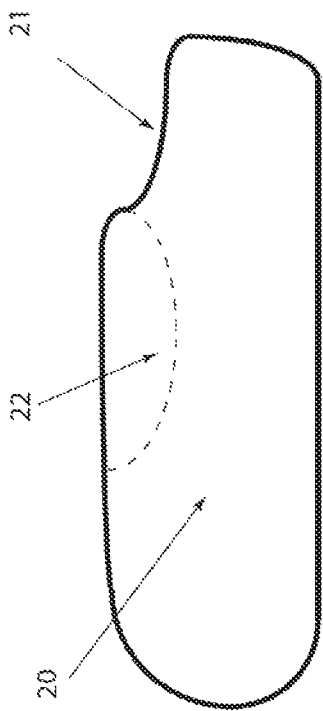
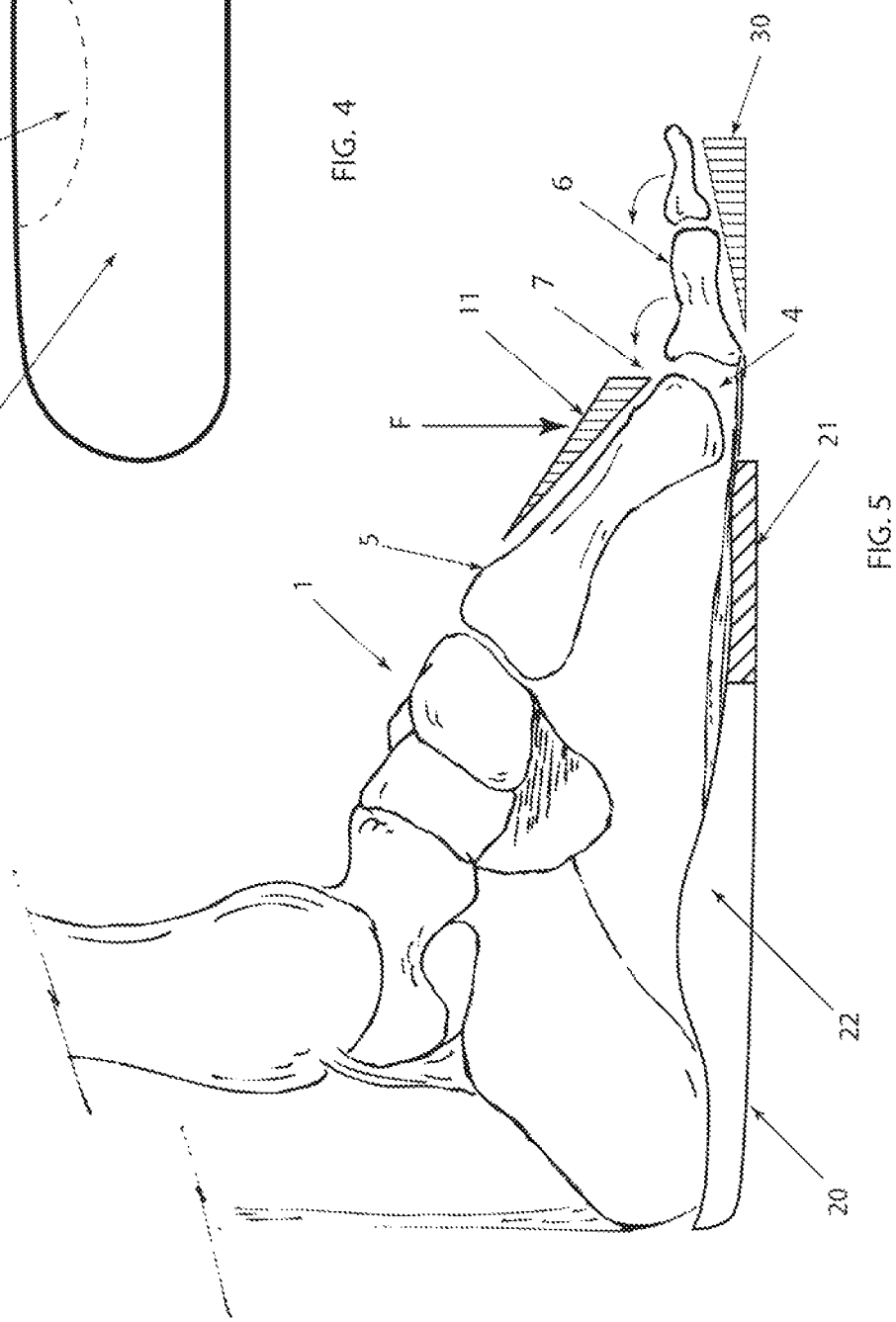

ORTHOTIC DEVICE AND METHOD OF USE

BACKGROUND OF THE INVENTION

1. Field of the Invention

The present invention relates generally to an orthotic support device for the forefoot, more particularly to an orthotic apparatus used to align and lock the first metatarsal in a plantarflexed position.

2. Description of the Prior Art

The foot is the base of the body, and for many years people have been trying to find the most effective way to stabilize the foot. Most of the efforts have been focused on the subtalar joint. However, of late, many ideas have been brought forth to bring the first metatarsal under control thus creating a stable foot and allowing control of the height of the arch.

The first metatarsal creates the distal part of the foot arch and has range of motion at the first metatarsal-cuneiform joint. This range of motion is often excessive; there is a condition known as functional hallux limitus in which the first metatarsal is hypermobile, raising the head of metatarsal bone above the base of the hallux, creating an inability of the hallux to dorsiflex, or bend while walking. The condition also creates a collapse of the arch, as well as, over-pronation, which can cause a wide variety of common foot, knee, hip, and lower back ailments. A solution to the problem is plantarflexing the first metatarsal so that the metatarsal head is lower than the base of the hallux, allowing free and unobstructed range of motion of the hallux, at the first metatarsal-phalangeal joint, which controls the functional hallux limitus. This is often attempted with a medial cut-out of an orthotic insole, either custom made or prefabricated. The orthotic device with a medial cut-out allows the head of the first metatarsal to drop lower than the other metatarsal heads, creating a steeper arch on the distal side, while the rest of the orthotic lifts the proximal part of the arch. Another pronation control device is the cluffy wedge, (U.S. Pat. No. 6,170,176, U.S. Pat. No. 6,874,258, U.S. Pat. No. 6,938,363 to James G. Clough), which pre-dorsiflexes the hallux to the top of the first metatarsal head and pushes the head down, plantarflexing the first metatarsal and keeping it from collapsing.

Many podiatric patients that could benefit by using an orthotic insole are intolerant of having the bottom of their foot manipulated, precluding the use of an insole with a medial cut-out. A major limitation of cluffy wedge embodiments and method of use, is the lack of space in conventional footwear to accommodate the wedge device and a permanently dorsiflexed hallux.

SUMMARY OF THE INVENTION

The present invention or metatarsal lock, is an orthotic apparatus positioned on the top of the forefoot that aligns and locks the first metatarsal in a plantarflexed position. A compressible orthotic pad is positioned on the forefoot directly over the first metatarsal. When pressure is applied to the orthotic, it keeps the distal portion of the arch in place, forces the first metatarsal down, while simultaneously unlocking the first metatarsal phalangeal joint and eliminating functional hallux limitus.

Pressure may be applied to the metatarsal lock by installing the apparatus on the wearer's foot and putting on a proper fitting shoe. The inside top surface of the shoe toebox will engage the top portion of the compressible pad and force the first metatarsal down into a plantarflexed position. The downward force may also be accomplished using a stretchable or elastic material band which encompasses the forefoot, or an adjustable band that fits snugly over the forefoot.

In one embodiment, the compressible metatarsal lock pad can be formed using a material such as neoprene, silicone, ethylene vinyl acetate (EVA), heat sensitive visco-elastic foam, foam rubber, cotton, wool felt, leather or other suitable known materials or a material yet to be developed. The pad is shaped to engage the length of the first metatarsal and may be an elongated oval, egg shaped, rectangular or trapezoidal. The pad may have a uniform thickness, or may be tapered from side to side, and or from top to bottom, having a thicker end proximate the first metatarsal head. The pad may also be cut, shaped, ground or skived by a podiatrist or qualified practitioner to adjust engagement with the first metatarsal, to enhance comfort and improve wearer compliance.

In another embodiment, the metatarsal lock pad can be a bladder filled with air or viscous material, such as water, oil, or silicone. In one embodiment the bladder size and rigidity may be adjusted by adding air, using a needle and pump, or by adding viscous material.

Each embodiment of the metatarsal lock may be used in conjunction with an orthotic having a cutout for the first ray and solid rearfoot control. Whereas, in the past orthotics with a first ray cutout only encouraged plantarflexion of the hallux; with the metatarsal lock, the compressible pad actually forces the first metatarsal into the cutout, providing excellent control of the first ray. The metatarsal lock may also be used in conjunction with a Cluffy wedge, or any number of other pronation control devices making them work more effectively.

In one embodiment, the metatarsal lock comprises an elastic material band having a pocket sewn on the top surface where a compressible metatarsal lock pad is installed. The compressible pad may be permanently sewn into the pocket or the pocket may open, allowing the pad to be removed for customization or to replace the pad with a different size or shape to better accommodate the wearer. In one embodiment, the band may include a fabric strap or compressible material rod attached to both the top and bottom surfaces of the band, the strap or rod will be positioned between the first and second phalanges (between the big toe and second toe) of the wearer, in a thong arrangement. The strap or rod helps the wearer properly position the compressible metatarsal lock pad over the first metatarsal ray, and insure proper alignment during extended use. In one embodiment, a separate pocket on the bottom surface of the band, extending from the second metatarsal ray to the lateral edge of foot, is also contemplated, allowing a podiatrist or the wearer to insert additional padding, or wedging, to adjust for different foot types, or medical conditions, and to ensure maximum wearer comfort. The elastic material band and compressible metatarsal lock pad provide support to the forefoot and downward deflection of the first metatarsal. However, for the metatarsal lock to fully engage the first metatarsal, the device is worn inside of properly fitting footwear. The construction and nature of the device is such that in can be worn under or over a conventional stocking and is small enough that it will not interfere with normal shoes or footwear.

One embodiment of the metatarsal lock may include an adjustable forefoot band. The band will include a pocket on the top surface, directly over the first metatarsal, for insertion of a compressible pad and may include additional pockets on the bottom surface of the forefoot band for further customization of the padding and to accommodate varying foot types and anomalous medical conditions. The adjustable band may overlap itself and attach using corresponding hook and loop fastener pads or in another embodiment, the band may include a clip where an end of the band is inserted and reversed over itself before being fastened. The level of forefoot support and deflection of the first metatarsal ray can be adjusted by releasing the book and loop fastener, providing tension on the tag end of the band and reattaching the tag end, effectively reducing the diameter of the forefoot band. The metatarsal lock with an adjustable forefoot band can be worn alone, under or over a stocking, and with most conventional footwear.

For another embodiment of the device, the metatarsal lock may include an adjustable forefoot band, having a closure mechanism and a pocket on the top surface of the forefoot directly over the first metatarsal for insertion of a compressible metatarsal lock pad. The adjustable band attached to an orthotic insole having a cutout for the first metatarsal ray, arch support and a formed heel cup. The device could be worn over or under a stocking and would be installed and adjusted by the wearer prior to installing a shoe.

Another embodiment of the metatarsal lock may be incorporated into a stocking, wherein, the stocking has a pocket sewn into the forefoot top surface for the insertion of a metatarsal lock pad or the metatarsal lock pad may be woven directly into the top surface of the stocking. The stocking has a defined heel portion and will be manufactured in a variety of sizes to provide proper alignment of the metatarsal lock pad. For effectiveness, pressure will be applied to the metatarsal lock pad by the inside top surface of a proper fitting shoe.

Another embodiment of the metatarsal lock device may be incorporated into a shoe or a sandal. A pocket for the compressible metatarsal lock can be formed into the inside top surface of a shoe or a sandal strap or can be formed integral with the inside surface of the footwear directly over the first metatarsal ray. It is contemplated that the shoe or sandal has an adjustable forefoot band that can be tensioned to engage the metatarsal lock pad. Tension could be supplied by, but not limited to, conventional lacing, isolated lacing for the forefoot only, a forefoot strap, or a cable ratchet mechanism. The shoe or sandal may have other pronation control mechanisms such as first metatarsal ray relief, a medial flange, toe wedge etc.

BRIEF DESCRIPTION OF DRAWINGS

FIG. 4 orthotic insole with first metatarsal ray cutout.
FIG. 5 partial anatomy of the foot showing engagement of a metatarsal lock and other orthotic accommodations.

DETAILED DESCRIPTION OF THE INVENTION

Figure 1:
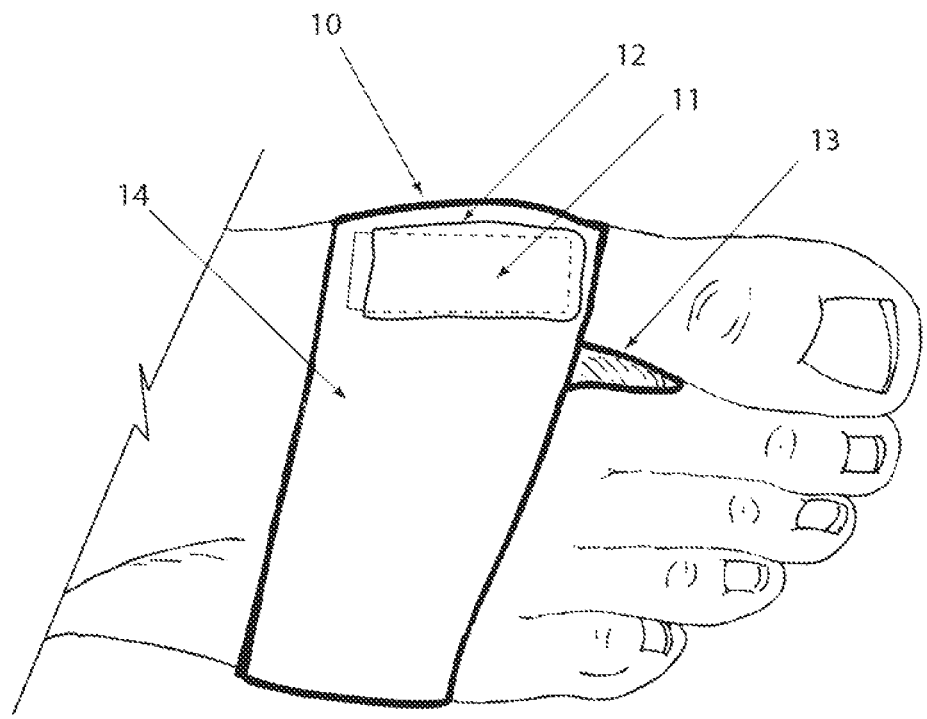
FIG. 1 metatarsal lock device on forefoot.

One embodiment of the metatarsal lock device 10 positioned on forefoot as shown and described in FIG. 1. The metatarsal lock 10 includes, an elastic material strap 14 that surrounds and supports the forefoot, a metatarsal lock pocket 12 formed in the top surface of the elastic strap 14, a metatarsal lock pad 11 is placed or formed into pocket 12. One embodiment may include a toe strap 13 which is positioned between the first and second phalanges of the wearer's foot. The toe strap 13 helps the wearer place the metatarsal lock pad 11 in the proper position, over the first metatarsal, when putting on the metatarsal lock device 10. Additionally, toe strap 13 keeps metatarsal lock pad 11 in proper position during activity and extended use. For one embodiment, pocket 12 is open on along at least one edge, or pocket 12 has a closeable flap, allowing metatarsal lock pad 11 to be removed and replaced with a different pad 11 or to allow the wearer or a podiatrist to remove the pad 11, modify the shape of pad 11 to better fit the wearer, and replace the pad 11 back into pocket 12. One embodiment may include a pocket (not shown) formed in the bottom surface of band 14, allowing the wearer to insert additional wedging or pads, to improve functionality of the device, to improve wearer comfort or to adjust for anatomical variations between wearers. In another embodiment, the diameter of the elastic material strap 14 is adjustable.

Figure 2:
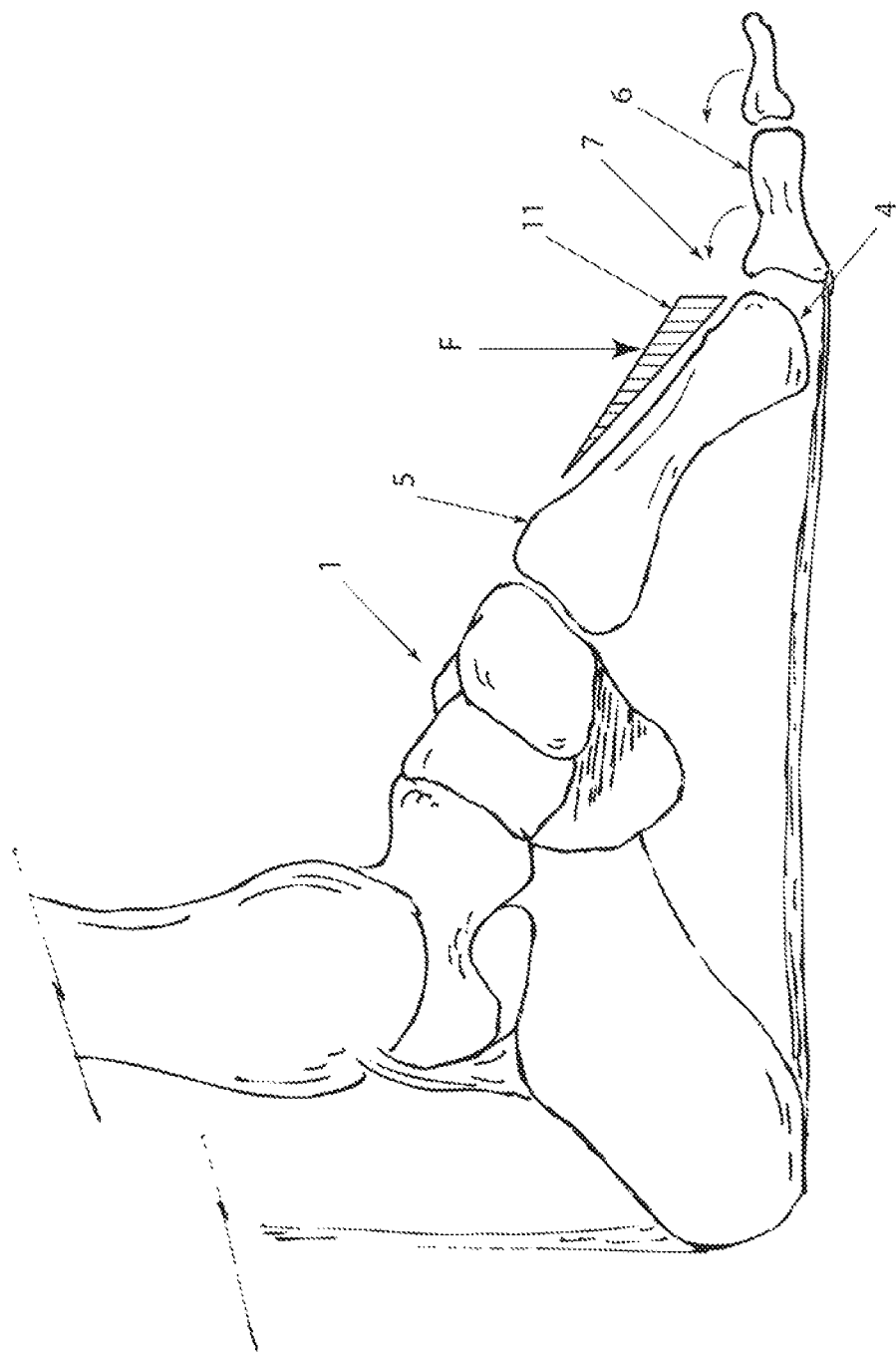
FIG. 2 partial anatomy of the foot showing engagement of a metatarsal lock.
Figure 3:
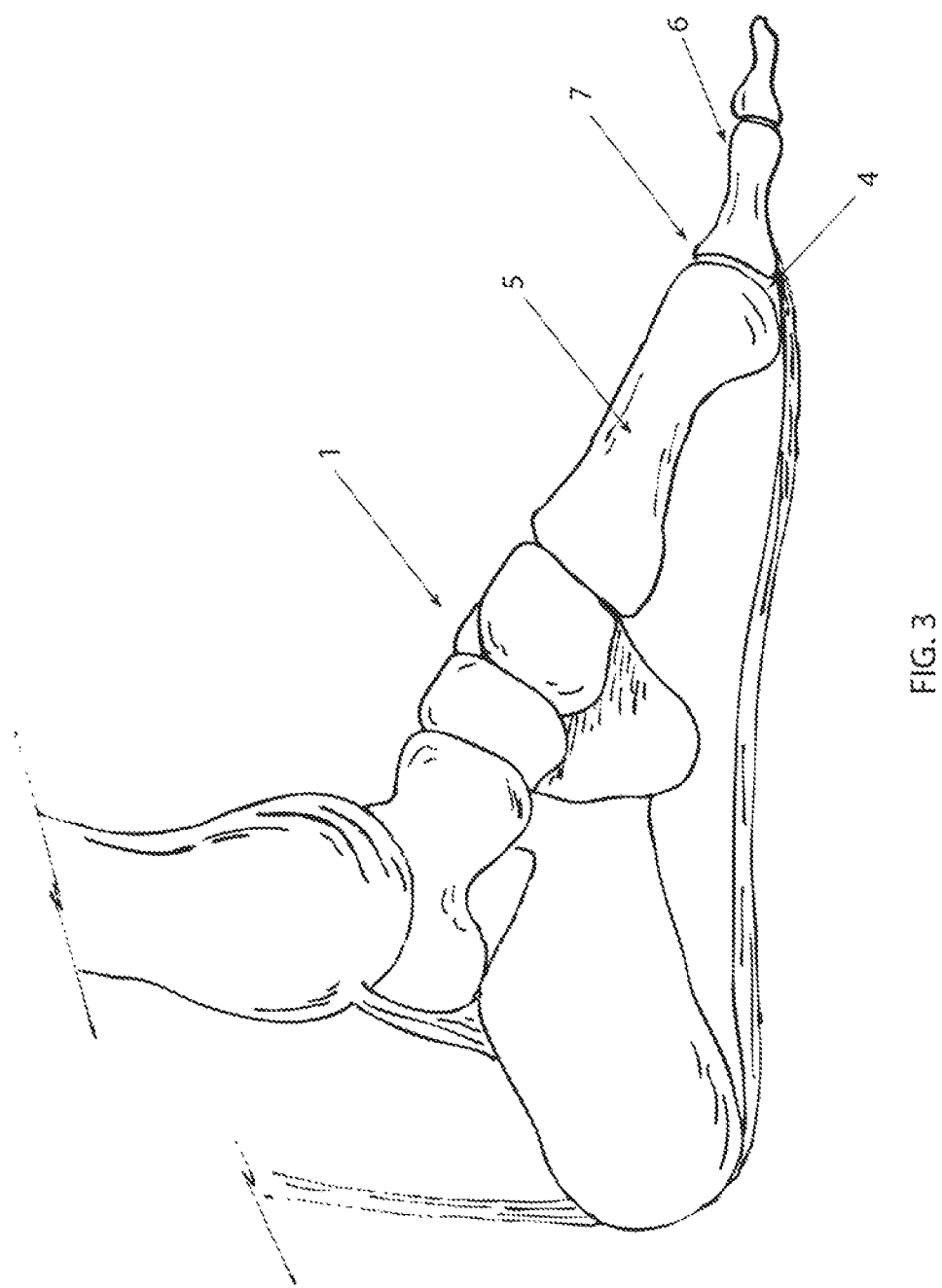
FIG. 3 partial anatomy of the foot showing functional hallux limitus.

The partial anatomy of a human foot 1 as shown in FIG. 2, including a first metatarsal 5, and the two bones comprising the hallux or big toe 6. A metatarsal lock pad 11 is disposed directly over the first metatarsal 5. When force F is applied to the top of pad 11, the metatarsal head 4 of the first metatarsal 5 is moved downward, opening the gap between the metatarsal 5 and the hallux 6, unlocking the first phalangeal joint 7, and allowing free unobstructed range of motion of the hallux 6. The partial anatomy of the human foot 1 in FIG. 3 shows the first metatarsal 5 in a substantially planer position with the metatarsal head 4 raised, causing restricted range of motion, or functional hallux limitus, between the first metatarsal head 4 and the hallux 6 at the first phalangeal joint 7.

One embodiment of the metatarsal lock 11 can be used in conjunction with other orthotic pronation control devices as shown in FIGS. 4 and 5. The metatarsal lock 11 transfers downward force F to the first metatarsal 5, dropping the first metatarsal head 4, unlocking the first phalangeal joint 7 and placing the hallux 6 in a dorsiflexed position. This position is achieved when using a metatarsal lock 11, even when the foot 1 is on a flat or substantially flat surface. However, if the metatarsal lock 11 is used in conjunction with an orthotic insole 20, having good rear foot control, arch support 22 and a first-ray cutout 21, the metatarsal lock 11 forces the first metatarsal 5 into the cut-out 21, steepening the drop of the first metatarsal head 4 and increases the release of the first phalangeal joint 7. The metatarsal lock 11 may also be used in conjunction with a Cluffy wedge 30.

The invention claimed is:

1. A foot orthotic device comprising:
   a pad sized to engage only the top portion of the first metatarsal bone;
   the pad being positioned on the foot directly over the first metatarsal bone;
   a force means engaging the pad, and means for assisting in the depression of the first metatarsal head into a plantar-flexed position, and,
   the force means is one of a strap, a sock and a shoe.

2. The foot orthotic device of claim 1, wherein the pad is one of rectangular, oval, egg-shaped, and trapezoidal.

3. The foot orthotic device of claim 1, wherein the pad has uniform thickness.

4. The foot orthotic device of claim 1, wherein the pad is a wedge.

5. The foot orthotic device of claim 1, wherein the pad is a bladder.

6. The foot orthotic device of claim 1, wherein the pad is a compressible material.

7. The foot orthotic device of claim 6, wherein the compressible material is one of rubber, foam rubber, visco-elastic foam, ethylene vinyl acetate, neoprene, silicone, cotton, wool felt, polyester and leather.

8. The foot orthotic device of claim 1, wherein the pad is positioned on the foot using a forefoot band having a bottom surface and a top surface, the top surface includes a pocket for installation of the pad.

9. The foot orthotic device of claim 8, wherein the pad is removably installed in the pocket.

10. The foot orthotic device of claim 8, wherein the forefoot band includes a pocket on the bottom surface.

11. The foot orthotic device of claim 8, wherein the forefoot band includes a toe strap.

12. The foot orthotic device of claim 8, wherein the forefoot band is adjustable.

13. The foot orthotic device of claim 8, wherein the forefoot band is attached to an orthotic insole.

14. The foot orthotic device of claim 1, wherein the pad is installed in a fitted sock.

15. The foot orthotic device of claim 1, wherein the pad is installed in a shoe.

16. A method for stabilizing the forefoot comprising:
  providing a pad sized to engage only the top portion of the first metatarsal bone;
  placing the pad over the first metatarsal bone;
  providing a force means of compressing the pad;
  compressing the pad;
  providing a means for assisting in the depression of the first metatarsal head into a plantarflexed position.

17. The method of claim 16, further comprising changing the pad for a second pad.

18. The method of claim 16, further comprising adjusting the compression of the pad.

19. The method of claim 16, wherein the force means is one of a strap, a sock and a shoe.

* * * * *